United States Patent
Laffitte et al.

(10) Patent No.: US 11,052,069 B2
(45) Date of Patent: Jul. 6, 2021

(54) REGIMES OF FXR AGONISTS

(71) Applicant: NOVARTIS AG, Basel (CH)

(72) Inventors: Bryan Laffitte, Cardiff, CA (US);
Andreas Bauer, Basel (CH); Michael Badman, Newton, MA (US); Jin Chen, Randolph, NJ (US); Patrick Mueller, Bottmingen (CH); Rachel Soon, Budd Lake, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 16/333,030

(22) PCT Filed: Sep. 12, 2017

(86) PCT No.: PCT/IB2017/055501
§ 371 (c)(1),
(2) Date: Mar. 13, 2019

(87) PCT Pub. No.: WO2018/051229
PCT Pub. Date: Mar. 22, 2018

(65) Prior Publication Data
US 2019/0262313 A1 Aug. 29, 2019

Related U.S. Application Data

(60) Provisional application No. 62/425,179, filed on Nov. 22, 2016, provisional application No. 62/394,463, filed on Sep. 14, 2016.

(51) Int. Cl.
*A61K 31/4162* (2006.01)
*A61K 31/4178* (2006.01)
*A61P 1/16* (2006.01)
*A61K 9/00* (2006.01)
*A61K 31/55* (2006.01)
*A61K 45/06* (2006.01)

(52) U.S. Cl.
CPC ........ *A61K 31/4162* (2013.01); *A61K 9/0053* (2013.01); *A61K 31/4178* (2013.01); *A61K 31/55* (2013.01); *A61P 1/16* (2018.01); *A61K 45/06* (2013.01)

(58) Field of Classification Search
CPC ........ A61K 31/4162; A61K 31/55; A61P 1/16
USPC ......................................................... 514/406
See application file for complete search history.

(56) References Cited

FOREIGN PATENT DOCUMENTS

| EP | 2289883 A1 * | 3/2011 | ........... C07D 413/04 |
| WO | 03/090745 A1 | 11/2003 | |
| WO | WO-2015069666 A1 * | 5/2015 | ........... C07D 231/54 |
| WO | 2016/040860 A1 | 3/2016 | |

OTHER PUBLICATIONS

Wang et al, Diabetes 2010, vol. 59, pp. 2916-2927. (Year: 2010).*

(Continued)

*Primary Examiner* — Craig D Ricci
*Assistant Examiner* — Janet L Coppins
(74) *Attorney, Agent, or Firm* — Emily T. Wu; Novartis Institues for BioMedical Reseach, Inc.

(57) ABSTRACT

The invention provides novel regimens of farnesoid X receptor (FXR) agonist and methods for modulating the activity of farnesoid X receptors (FXRs) using novel regimes of specific FXR agonists, in particular for treating or preventing fibrotic or cirrhotic diseases or disorders, such as liver diseases.

6 Claims, 2 Drawing Sheets

(56) References Cited

OTHER PUBLICATIONS

Ahmad H. Ali et al. "Recent advances in the development of farnesoid X receptor agonists", Annals of Translational Medicine, vol. 3, No. 1, Jan. 2015, pp. 1-16.
Luciano Adorini et al. "Farnesoid X receptor targeting to treat nonalcoholic steatohepatitis", Drug Discovery Today, vol. 17., No. 17-18, Sep. 1, 2012, pp. 988-997.
Schwab P. et al. "G18: The FXR agonist PX20606 reduces liver damage, fibrosis and portal hypertension in cirrhotic rats", Journal of Hepatology, vol. 62, Apr. 2015, p. S238.
Jiang et al., "Farnesoid X Receptor Modulates Renal Lipid Metabolism, Fibrosis, and Diabetic Nephropathy", Diabetes, Oct. 2007, pp. 2485-2493, vol. 56, No. 10.
V.G. Belikov, "Relationship between the chemical structure, properties of substances and their effect on the body", Pharmaceutical Chemistry, M.: MEDpress-inform, 2.6, 2007, pp. 27-29.
M.D. Mashkovskiy "Interaction between the medicaments", Drugs, 14th edition, vol. 1, Moscow, 2001, p. 11.

\* cited by examiner

Figure 2 : NAFLD Activity Score of Compound A and OCA.
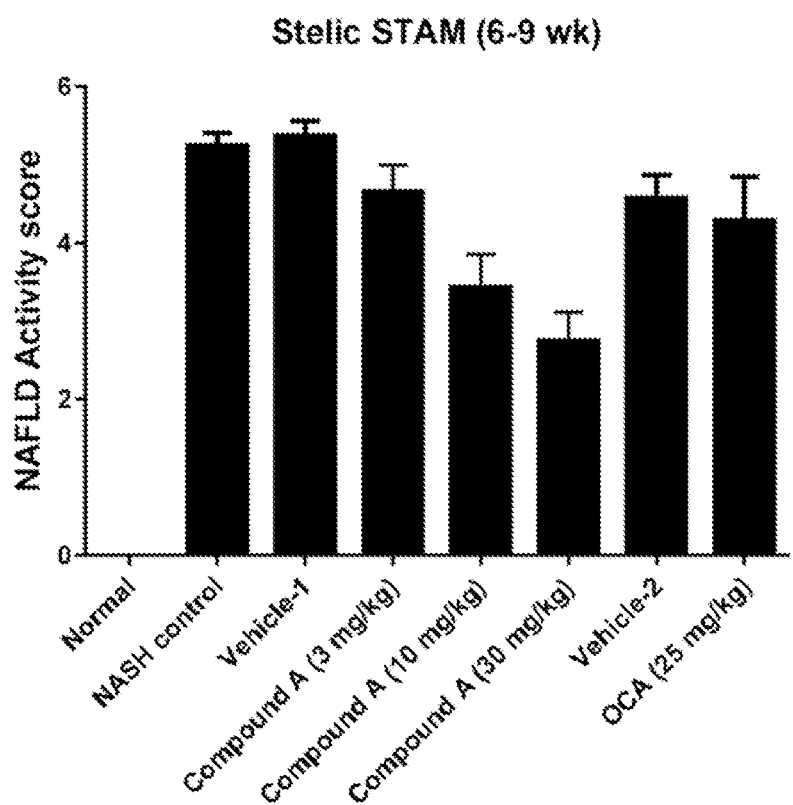

REGIMES OF FXR AGONISTS

This application is a 371 U.S. national phase application of international application number PCT/IB2017/055501 filed 12 Sep. 2017, which application claims priority to U.S. provisional patent application No. 62/394,463 filed 14 Sep. 2016; and to U.S. provisional patent application Ser. No. 62/425,179 filed 22 Nov. 2016. Each of these applications is incorporated herein by reference in its entirety and for all purposes.

FIELD OF THE INVENTION

The present invention relates to novel regimens of farnesoid X receptor (FXR) agonist, as well as methods, uses, compositions involving such regimens. Furthermore, the invention is directed to the use of a FXR agonist for treating or preventing fibrotic or cirrhotic diseases or disorders, e.g. liver diseases or disorders.

BACKGROUND OF THE INVENTION

Farnesoid X Receptor Agonist (FXR) is a nuclear receptor activated by bile acids, also known as Bile acid Receptor (BAR). FXR is expressed in principal sites of bile acid metabolism, such as liver, intestine and kidney, where it mediates effects on multiple metabolic pathways in a tissue-specific manner.

The mode of action of FXR in the liver and intestine is well known, and described e.g. in (Calkin and Tontonoz, (2012), Nature Reviews Molecular Cell Biology 13, 213-24). FXR is responsible for modulating bile acid production, conjugation and elimination through multiple mechanisms in the liver and intestine. In normal physiology, FXR detects increased levels of bile acids and responds by decreasing bile acid synthesis and bile acid uptake while increasing bile acid modification and secretion in the liver. In the intestine, FXR detects increased bile acid levels and decreases bile acid absorption and increases secretion of FGF15/19. The net result is a decrease in the overall levels of bile acids. In the liver, FXR agonism increases expression of genes involved in canalicular and basolateral bile acid efflux and bile acid detoxifying enzymes while inhibiting basolateral bile acid uptake by hepatocytes and inhibiting bile acid synthesis.

Furthermore, FXR agonists decrease hepatic triglyceride synthesis leading to reduced steatosis, inhibit hepatic stellate cell activation reducing liver fibrosis and stimulate FGF15/FGF19 expression (a key regulator of bile acid metabolism) leading to improved hepatic insulin sensitivity. Thus, FXR acts as a sensor of elevated bile acids and initiates homeostatic responses to control bile acid levels, a feedback mechanism that is believed to be impaired in cholestasis. FXR agonism has shown clinical benefits in subjects with cholestatic disorders (Nevens et al., J. Hepatol. 60 (1 SUPPL. 1): 347A-348A (2014)), bile acid malabsorption diarrhea (Walters et al., Aliment Pharmacol. Ther. 41(1):54-64 (2014)) and non-alcoholic steatohepatitis (NASH; Neuschwander-Tetri et al 2015).

Bile acids are normally produced by the organism. At high dose they can cause different side effects as they have detergent properties (diarrhea or cellular injury). In addition, they can also cause pruritus.

Nonalcoholic fatty liver disease (NAFLD) is the most common cause of chronic liver disease in the Western world (Ratziu et al 2010). NASH includes fat accumulation in the liver, as well as inflammation which over time can lead to increasing fibrosis, cirrhosis and end stage liver disease. Liver transplantation is the only treatment for advanced cirrhosis with liver failure, and transplantation is increasingly performed in persons suffering from NASH.

Estimates of the worldwide prevalence of NAFLD range from 6.3% to 33% with a median of 20% in the general population. The estimated prevalence of NASH is lower, ranging from 3 to 5% (Younossi et al., Hepatology, Vol. 64, No. 1, 2016). NASH is a worldwide problem with growing prevalence over the last few decades. Over the last decade NASH has risen from uncommon to the second indication for liver transplantation in the US. It is expected to be the leading cause of transplant by 2020 (Wong, et al, Gastro 2015). NASH is highly associated with the metabolic syndrome and Type 2 diabetes mellitus. NASH is a cause of progressive fibrosis and of cirrhosis. Cirrhosis due to NASH increases the risk of hepatocellular carcinoma and hepatocellular cancer. Furthermore, cardiovascular mortality is an important cause of death in NASH patients.

Chronic cholestasis and liver inflammation are the two main pathophysiological components of the two major classes of disease—primary biliary cirrhosis (PBC) and primary sclerosing cholangitis (PSC)—leading to bile duct destruction and ultimately to cirrhosis and liver failure. Liver transplantation appears to be the only life-saving procedure.

Ursodeoxycholic acid (UCDA), also known as ursodiol, is the main treatment for PBC. UCDA is a secondary bile acid, i.e. it is metabolized from a primary bile acid (produced by the liver) by intestinal bacteria, after the primary acid has been secreted into the intestine. UDCA is not an FXR agonist.

UDCA halts progression in many patients, but in about 30-40% of the population do not respond. Since May 2016, another molecule has been approved in the US for the treatment of PBC, when combined with UDCA for primary biliary cholangitis (PBC) in adult patients with an inadequate response to UDCA, or as a single therapy in adults unable to tolerate UDCA. This new molecule is Obeticholic acid (OCA), a bile-acid mimetic. OCA is a FXR agonist.

Currently there is no approved therapy for NASH.

There remains a need for efficacious treatments and therapies for liver conditions mediated by FXR, in particular liver diseases such as NAFLD, NASH or PBC, and for late stage liver diseases.

Development of NASH, involves several mechanisms: accumulation of fat in the liver (steatosis), inflammation of the liver, hepatocyte ballooning, and fibrosis. The NAFLD Activity Score (NAS) was developed as a tool to measure changes in NAFLD during therapeutic trials. The score is calculated as the unweighted sum of the scores for steatosis (0-3), lobular inflammation (0-3), and ballooning (0-2).

For preventing or treating such diseases or disorders, a medicament would be particularly efficient if it has an impact on each of these different aspects.

In a clinical trial aimed at evaluating the efficacy and safety of cenicriviroc (a CCR2/5 inhibitor) for the treatment of NASH in adults with liver fibrosis, the treatment with cenicriviroc shown a reduction of fibrosis but no significant impact on the improvement of NAS. Furthermore cenicriviroc can induce fatigue or diarrhea in a small part of the patients (see "Tobira Therapeutics Announces Clinically and Statistically Significant Improvement in Liver Fibrosis from Phase 2b CENTAUR NASH Trial at One Year" Jul. 25, 2016).

When tested in nonalcoholic steatohepatitis patients, obeticholic acid showed efficacy, in particular a significant improvement in NAS, i.e. strong impact on steatosis with additional effects on inflammation and ballooning. But OCA long term administration raises safety concerns because it can be associated with pruritus, as well as with increased LDL cholesterol (see "Intercept Announces New FLINT Trial Data Showing OCA Treatment Increases Fibrosis Resolution and Cirrhosis Prevention in High-Risk NASH Patients", Apr. 23, 2015). To avoid the risk of adverse cardiovascular events, concomitant administration of statins may be required for long term treatment of NASH patients.

Therefore there is a need to provide treatments for fibrotic/cirrhotic diseases or disorders, e.g. liver diseases or disorders, that can address the different aspects of these complex conditions, while demonstrating an acceptable safety and/or tolerability profile.

SUMMARY OF THE INVENTION

The invention provides methods of treating, preventing, or ameliorating conditions mediated by farnesoid X receptors (FXR), in particular liver diseases, comprising administering to a subject in need thereof a therapeutically effective amount of a FXR agonist.

According to the invention, the FXR agonist is a 4-((N-benzyl-8-chloro-1-methyl-1,4-dihydrochromeno[4,3-c]pyrazole-3 carboxamido)methyl)benzoic acid (Compound A), a pharmaceutically acceptable salt, solvate, prodrug, ester and/or an amino acid conjugate thereof, e.g. the meglumine salt. Compound A is a non-bile acid derived FXR agonist.

The invention provides new dosing regimens of Compound A as herein defined (e.g. in free form or a pharmaceutically acceptable salt thereof, e.g. meglumine salt), for treating or preventing fibrotic or cirrhotic diseases or disorders, e.g. liver diseases and disorders, comprising Compound A as herein defined, at a dose (e.g. daily dose) in a range of about 15 mg to about 250 mg, e.g. about 20 mg to about 250 mg, e.g. about 25 mg to about 250 mg, e.g about 30 mg to about 250 mg, e.g about 50 mg to about 250 mg, e.g. about 100 mg to about 250 mg, e.g. about 10 mg to about 200 mg; e.g. about 100 mg to about 200 mg; e.g. about 30 mg to about 200 mg, e.g. about 50 mg to about 200 mg.

The invention further provides new dosing regimens of FXR agonists of formula (I), e.g. Compound A as herein defined, for treating or preventing liver diseases and disorders mediated by farnesoid X receptors (FXR), as well as the use of such new regimens and pharmaceutical compositions adapted for administering such new regimens. Such new dosing regimens are effective and well tolerated regimens for treating or preventing liver diseases and disorders mediated by farnesoid X receptors (FXR) in humans.

The invention further provides new dosing regimens of Compound A as herein defined (e.g. in free form or a pharmaceutically acceptable salt thereof, e.g. meglumine salt, at a dose (e.g. daily dose) e.g. about 15 mg, e.g. about 20 mg, e.g. about 25 mg, e.g. about 30 mg, e.g. about 50 mg, e.g. about 60 mg, e.g about 80 mg, e.g. about 100 mg, e.g. about 120 mg, e.g. about 140 mg, e.g. about 150 mg, e.g about 180 mg, e.g about 200 mg, e.g about 220 mg, e.g about 250 mg.

The invention further provides therapeutic regimens for treating or preventing a condition mediated by Farnesoid X receptor (FXR), comprising administering Compound A as herein defined (e.g. in free form or a pharmaceutically acceptable salt thereof, e.g. meglumine salt), at a dose of about 15 mg, e.g. about 20 mg, e.g. about 25 mg, e.g. about 30 mg, e.g. about 50 mg, e.g. about 60 mg, e.g about 80 mg, e.g. about 100 mg, e.g. about 120 mg, e.g. about 140 mg, e.g. about 150 mg, e.g about 180 mg, e.g about 200 mg, e.g about 220 mg, e.g about 250 mg. Such doses may be for daily administration (e.g. daily doses).

The invention further provides therapeutic regimens for treating or preventing a condition mediated by Farnesoid X receptor (FXR), comprising administering Compound A as herein defined (e.g. in free form or a pharmaceutically acceptable salt thereof, e.g. meglumine salt), at a dose of about e.g. about 15 mg, e.g. about 25 mg, e.g. about 50 mg, e.g. about 100 mg, e.g. about 150 mg, e.g about 200 mg, e.g about 250 mg. Such doses may be for daily administration (e.g. daily doses).

Furthermore the invention provides a method for treating or preventing a condition mediated by Farnesoid X receptor (FXR) in a subject suffering therefrom, comprising administering to the subject Compound A as herein defined (e.g. in free form or a pharmaceutically acceptable salt thereof, e.g. meglumine salt); wherein said FXR agonist is to be administered at a daily dose of about 15 mg, e.g. about 20 mg, e.g. about 25 mg, e.g. about 30 mg, e.g. about 50 mg, e.g. about 60 mg, e.g about 80 mg, e.g. about 100 mg, e.g. about 120 mg, e.g. about 140 mg, e.g. about 150 mg, e.g about 180 mg, e.g about 200 mg, e.g about 220 mg, e.g about 250 mg. Such doses may be for daily administration (e.g. daily doses).

A method for treating or preventing a condition mediated by Farnesoid X receptor (FXR) in a subject suffering therefrom, wherein the condition is a chronic liver disease, such as e.g. non-alcoholic fatty liver disease (NAFLD), non-alcoholic steatohepatitis (NASH), drug-induced bile duct injury, gallstones, liver cirrhosis, alcohol-induced cirrhosis, cystic fibrosis, bile duct obstruction, cholelithiasis, or liver fibrosis and wherein said FXR agonist is to be administered at a daily dose of about 15 mg, e.g. about 20 mg, e.g. about 25 mg, e.g. about 30 mg, e.g. about 50 mg, e.g. about 60 mg, e.g about 80 mg, e.g. about 100 mg, e.g. about 120 mg, e.g. about 140 mg, e.g. about 150 mg, e.g about 180 mg, e.g about 200 mg, e.g about 220 mg, e.g about 250 mg. Such doses may be for daily administration (e.g. daily doses).

The invention further provides new dosing regimens of Compound A as herein defined (e.g. in free form or a pharmaceutically acceptable salt thereof, e.g. meglumine salt), for treating or preventing fibrotic or cirrhotic diseases or disorders, e.g. liver diseases and disorders, comprising Compound A as herein defined, at a dose (e.g. daily dose) about 50 mg, e.g. about 60 mg, e.g about 80 mg, e.g. about 100 mg, e.g. about 120 mg, e.g. about 140 mg, e.g. about 150 mg, e.g about 180 mg, e.g about 200 mg, e.g about 220 mg, e.g about 250 mg.

Furthermore the invention provides new dosing regimens of Compound A as herein defined (e.g. in free form or a pharmaceutically acceptable salt thereof, e.g. meglumine salt), for treating or preventing fibrotic or cirrhotic diseases or disorders, e.g. liver diseases and disorders, comprising administering the Compound A as herein defined, at a dose of about 50 mg/day, e.g. about 60 mg/day, e.g about 80 mg/day, e.g. about 100 mg/day, e.g. about 120 mg/day, e.g. about 140 mg/day, e.g. about 150 mg/day, e.g. about 180 mg/day, e.g. about 200 mg/day, e.g. about 220 mg/day, e.g. about 250 mg/day.

The invention further provides new dosing regimens of Compound A as herein defined for treating or preventing non-alcoholic steatohepatitis (NASH), wherein NASH is confirmed based on liver biopsy obtained 2 years or less before treatment initiation with Compound A (also called biopsy-proven NASH) and NASH is mild to moderate with fibrosis level F2-F3.

The invention further provides new dosing regimens of Compound A as herein defined for treating or preventing non-alcoholic steatohepatitis (NASH) which show improvement of liver functional tests including surrogates of clinical decompensation (MELD and CPT) in subjects with MELD>15 after 3 months/48 weeks/72 weeks. The new dosing regimens of Compound show at least 1 stage of fibrosis improvement in patients with fibrosis (F1-F3) as compared to patients in the placebo group. The new dosing regimens of Compound show at least one stage of liver fibrosis improvement with no worsening of NASH in patients.

Furthermore the invention provides new dosing regimens of Compound A as herein defined (e.g. in free form or a pharmaceutically acceptable salt thereof, e.g. meglumine salt), for treating or preventing fibrotic or cirrhotic diseases or disorders, e.g. liver diseases and disorders, comprising administering the Compound A as herein defined, at a dose of about 50 mg twice daily, about 60 mg twice daily, about 80 mg twice daily, about 100 mg twice daily, about 140 mg twice daily, about 150 mg twice daily, about 180 mg twice daily, about 200 mg twice daily, about 220 mg twice daily, about 250 mg twice daily.

Furthermore the invention provides a pharmaceutical unit dosage form compositions comprising about 15 mg, about 20 mg, about 25 mg, about 50 mg, about 100 mg of Compound A suitable for oral administration. Such unit dosage form compositions may be in a form selected from a liquid, a tablet, a capsule. Also these unit dosage form compositions are for use in treating or preventing a condition mediated by FXR; disorder, wherein said condition mediated by FXR is non-alcoholic fatty liver disease (NAFLD), non-alcoholic steatohepatitis (NASH), drug-induced bile duct injury, gallstones, liver cirrhosis, alcohol-induced cirrhosis, cystic fibrosis, bile duct obstruction, cholelithiasis, liver fibrosis.

Also these unit dosage form compositions are for use in treating a disorder selected from the group consisting of cholestasis (e.g. intrahepatic cholestasis, estrogen-induced cholestasis, drug-induced cholestasis, cholestasis of pregnancy, parenteral nutrition-associated cholestasis), primary biliary cholangitis (PBC), cirrhosis, primary sclerosing cholangitis (PSC), progressive familiar cholestatis (PFIC), Alagille syndrome, biliary atresia, ductopenic liver transplant rejection and cystic fibrosis liver disease; e.g. primary biliary cholangitis (PBC).

In some aspects, the invention provides administering Compound A as herein defined (e.g. in free form or a pharmaceutically acceptable salt thereof, e.g. meglumine salt), with an additional therapeutic agent, either simultaneously, sequentially or separately, e.g. in any order. For example the additional therapeutic agent is with a therapeutic agent for the treatment of obesity, metabolic syndrome, cholesterol disorders or cardiometabolic diseases including diabetes, insulin resistance, dyslipidemia.

In some aspects, the additional therapeutic agent is a CCR2/5 inhibitor, e.g. CVC, a pharmaceutically acceptable salt, solvate, prodrug and/or ester thereof, e.g. CVC, e.g. cenicriviroc mesylate.

There is also provided pharmaceutical combinations containing, separately or together, (i) Compound A as herein defined (e.g. in free form or a pharmaceutically acceptable salt thereof, e.g. meglumine salt) (ii) an additional therapeutic agent, e.g. a CCR2/5 inhibitor, e.g. cenicriviroc, or a pharmaceutically acceptable salt, prodrug or solvate thereof, e.g. cenicriviroc mesylate, for simultaneous, sequential or separate administration.

In some aspects, the pharmaceutical combination is a fixed combination, e.g. a fixed combination comprising (i) Compound A as herein defined (e.g. in free form or a pharmaceutically acceptable salt thereof, e.g. meglumine salt, and (ii) an additional therapeutic agent, e.g. a CCR2/5 inhibitor, e.g. cenicriviroc (as herein defined, e.g. in free form or as a pharmaceutically acceptable salt thereof, e.g. cenicriviroc mesylate).

In some aspects, Compound A as herein defined (e.g. in free form or a pharmaceutically acceptable salt thereof, e.g. meglumine salt) is for use in the prevention or treatment of a fibrotic or cirrhotic disease or disorder, e.g. a liver disease or disorder, e.g. a chronic liver disease or disorder, e.g a disease or disorder selected from the group consisting of cholestasis, intrahepatic cholestasis, estrogen-induced cholestasis, drug-induced cholestasis, cholestasis of pregnancy, parenteral nutrition-associated cholestasis, primary biliary cirrhosis (PBC), primary sclerosing cholangitis (PSC), progressive familiar cholestasis (PFIC), non-alcoholic fatty liver disease (NAFLD), non-alcoholic steatohepatitis (NASH), drug-induced bile duct injury, gallstones, liver cirrhosis, alcohol-induced cirrhosis, cystic fibrosis-associated liver disease (CFLD), bile duct obstruction, cholelithiasis, liver fibrosis, renal fibrosis, dyslipidemia, atherosclerosis, diabetes, diabetic nephropathy, colitis, newborn jaundice, prevention of kernicterus, veno-occlusive disease, portal hypertension, metabolic syndrome, hypercholesterolemia, intestinal bacterial overgrowth, erectile dysfunction, progressive fibrosis of the liver caused by any of the diseases above or by infectious hepatitis, e.g. NAFLD, NASH, hepatic fibrosis, hepatosteatis or PBC.

In other aspects of the invention, Compound A as herein defined (e.g. in free form or a pharmaceutically acceptable salt thereof, e.g. meglumine salt), and optionally an additional therapeutic agent, e.g. CVC as herein defined, are provided for slowing, arresting, or reducing the development of a cirrhotic disease or disorder, e.g. chronic liver disease or disorder, e.g. NAFLD, NASH, liver fibrosis and PBC.

In yet another aspect, Compound A as herein defined (e.g. in free form or a pharmaceutically acceptable salt thereof, e.g. meglumine salt), and optionally an additional therapeutic agent, e.g. CVC as herein defined, are provided for preventing or delaying progression of a chronic liver disease or disorder to a more advanced stage or a more serious condition thereof, e.g for preventing or delaying progression of a chronic liver disease or disorder selected from the group consisting of NAFLD, NASH, hepatic fibrosis and PBC.

Furthermore, the invention relates to the use of Compound A as herein defined (e.g. in free form or a pharmaceutically acceptable salt thereof, e.g. meglumine salt), and optionally an additional therapeutic agent, e.g. CVC as herein defined, in methods of treating, preventing or ameliorating a fibrotic or cirrhotic disease or disorder, e.g a liver disease or disorder. In some aspects, such methods comprise administering to a subject in need thereof Compound A and the additional therapeutic agent, e.g. a CCR2/5 inhibitor, e.g. cenicriviroc (in free form or as a pharmaceutically acceptable salt, solvate, prodrug, and/or ester thereof, e.g. cenicriviroc mesylate), each being in an amount that is jointly therapeutically effective.

There is provided the use of, Compound A as herein defined (e.g. in free form or a pharmaceutically acceptable salt thereof, e.g. meglumine salt), and optionally an additional therapeutic agent, e.g. CVC as herein defined, optionally in combination, e.g. fixed or free combination, with one or more additional therapeutic agent, e.g. a CCR2/5 inhibitor e.g. cenicriviroc (or a pharmaceutically acceptable salt, solvate, prodrug and/or ester thereof, e.g. cenicriviroc mesylate), for the manufacture of a medicament for the prevention or treatment of a liver disease or disorder, e.g. a liver disease or disorder selected from the group consisting of NAFLD, NASH, hepatosteatosis, liver fibrosis, cirrhosis, PBC.

There is also provided pharmaceutical combinations for preventing, delaying or treating a liver disease or disorder, wherein Compound A as herein defined (e.g. in free form, or a pharmaceutically acceptable salt thereof, e.g. meglumine salt), and (ii) a CCR2/5 inhibitor e.g. cenicriviroc (in free form or as a pharmaceutically acceptable salt, solvate, prodrug and/or ester thereof, e.g. cenicriviroc mesylate).

In some aspects of the invention, there is provided pharmaceutical combinations for preventing, delaying or treating a chronic liver disease or disorder, e.g. selected from the group consisting of steatosis, NASH, fibrosis and cirrhosis, e.g. steatosis, NASH and/or fibrosis, wherein the combination comprises (i) Compound A as herein defined (e.g. in free form or a pharmaceutically acceptable salt thereof, e.g. meglumine salt), and (ii) a CCR2/5 inhibitor e.g. cenicriviroc (in free form or as a pharmaceutically acceptable salt, solvate, prodrug and/or ester thereof, e.g. in free form or as a pharmaceutically acceptable salt thereof, e.g. cenicriviroc mesylate).

There is further provided pharmaceutical combinations comprising (i) Compound A as herein defined (e.g. in free form or a pharmaceutically acceptable salt thereof, e.g. meglumine salt), and (ii) a CCR2/5 inhibitor e.g. cenicriviroc (in free form or as a pharmaceutically acceptable salt, solvate, prodrug, and/or ester thereof, e.g. in free form or as a pharmaceutically acceptable salt thereof, e.g. cenicriviroc mesylate), for preventing, delaying or treating NASH.

Furthermore, there is also provided pharmaceutical combinations comprising (i) Compound A as herein defined (e.g. in free form or a pharmaceutically acceptable salt thereof, e.g. meglumine salt), and (ii) a CCR2/5 inhibitor e.g. cenicriviroc (in free form or as a pharmaceutically acceptable salt, solvate, prodrug, and/or ester thereof, e.g. in free form or as a pharmaceutically acceptable salt thereof, e.g. cenicriviroc mesylate), for preventing, delaying or treating liver fibrosis.

There is also provided pharmaceutical combinations comprising (i) Compound A as herein defined (e.g. in free form or a pharmaceutically acceptable salt thereof, e.g. meglumine salt), and (ii) a CCR2/5 inhibitor e.g. cenicriviroc (in free form or as a pharmaceutically acceptable salt, solvate, prodrug, and/or ester thereof, e.g. in free form or as a pharmaceutically acceptable salt thereof, e.g. cenicriviroc mesylate), for preventing, delaying or treating hepatosteatosis.

There is further provided pharmaceutical combinations comprising (i) Compound A as herein defined (e.g. in free form or a pharmaceutically acceptable salt thereof, e.g. meglumine salt), and (ii) a CCR2/5 inhibitor e.g. cenicriviroc (in free form or as a pharmaceutically acceptable salt, solvate, prodrug, and/or ester thereof, e.g. in free form or as a pharmaceutically acceptable salt thereof e.g. cenicriviroc mesylate), for preventing, delaying or treating hepatocellular ballooning.

There is also provided pharmaceutical combinations comprising (i) Compound A, as herein defined, e.g. in free form or as a pharmaceutically acceptable salt thereof), and (ii) a CCR2/5 inhibitor e.g. cenicriviroc (in free form or as a pharmaceutically acceptable salt, solvate, prodrug, and/or ester thereof, e.g. in free form or as a pharmaceutically acceptable salt thereof, e.g. cenicriviroc mesylate), for preventing, delaying or treating PBC.

A further aspect of the present invention is a method for the treatment, delaying or prevention of a fibrotic disease or disorder, e.g. a liver disease or disorder, e.g. chronic liver disease or disorder, comprising administering a therapeutically effective amount of combination of (i) Compound A as herein above defined (e.g. in free form or a pharmaceutically acceptable salt thereof, e.g. meglumine salt), and (ii) an additional therapeutic agent, as herein defined, e.g. a CCR2/5, e.g. cenicriviroc (in free form or as a pharmaceutically acceptable salt, solvate, prodrug, and/or ester thereof, e.g. in free form or as a pharmaceutically acceptable salt thereof), and a pharmaceutically acceptable carrier to a subject in need of such treatment. A therapeutically effective amount of each of the component of the combination of the present invention may be administered simultaneously or sequentially and in any order.

In other embodiments, there are provided pharmaceutical combinations, containing, separate or together, (i) Compound A as herein defined, e.g. in free form or a pharmaceutically acceptable salt thereof; and (ii) a CCR2/5 inhibitor, e.g. cenicriviroc (as hereinabove defined, e.g. in free form or as a pharmaceutically acceptable salt thereof), for simultaneous or sequential administration, wherein the ratio (mg/mg) of Compound A to CCR2/5 inhibitor, e.g. cenicriviroc (as hereinabove defined), is about 0.5:1 to about 10:1, e.g. about 1:1 to about 3:1.

In other embodiments, there are provided: use, a FXR agonist or a method according to any one of the above listed embodiments, for treating or preventing a liver disease or disorder selected from non-alcoholic fatty liver disease (NAFLD), non-alcoholic steatohepatitis (NASH), drug-induced bile duct injury, gallstones, liver cirrhosis, alcohol-induced cirrhosis, cystic fibrosis, bile duct obstruction, cholelithiasis and liver fibrosis.

In other embodiments, there are provided: any of use, a FXR agonist or a method listed above, for treating or preventing non-alcoholic steatohepatitis (NASH), wherein NASH is confirmed based on liver biopsy obtained 2 years or less before treatment initiation with Compound A (also called biopsy-proven NASH) and NASH is mild to moderate with fibrosis level F2-F3. Alternatively, the presence of NASH has been demonstrated by:

i) by one of the following: Histologic evidence of NASH based on liver biopsy obtained 2 years or less before treatment with a FXR agonist, e.g Compound A as defined herein, with a diagnosis consistent with NASH, fibrosis level F1, F2 or F3, no diagnosis of alternative chronic liver diseases and ALT 60 IU/L (males) or 40 IU/L (females), or ii) Phenotypic diagnosis of NASH based on presence of all three of the following:

ALT≥60 IU/L (males) or ≥40 IU/L (females) and

BMI≥27 kg/m2 (in patients with a self-identified race other than Asian) or ≥23 kg/m2 (in patients with a self-identified Asianrace) and Diagnosis of Type 2 diabetes mellitus by having either: HbA1C≥6.5% or Drug therapy for Type 2 diabetes mellitus.

Various (enumerated) embodiments of the invention are described herein. It will be recognized that features specified in each embodiment may be combined with other specified features to provide further embodiments of the present invention.

DESCRIPTION OF THE FIGURES

FIGS. 1 and 2 describe an in-vivo efficacy study of Compound A versus OCA in the STAM model of nonalcoholic steatohepatitis for a treatment period of 6-9 weeks. FIG. 2 refers to the results on NAFLD Activity Score; FIG. 1 to Sirius-red positive area.

DETAILED DESCRIPTION OF THE INVENTION

Definitions

Figure 1:
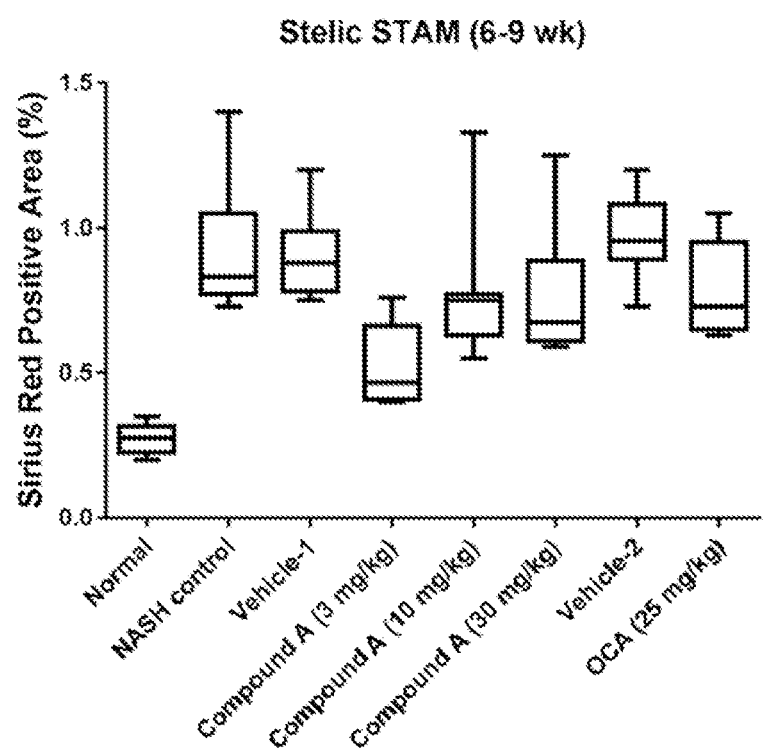

For purposes of interpreting this specification, the following definitions will apply and whenever appropriate, terms used in the singular will also include the plural and vice versa.

As used herein, the term "about" in relation to a numerical value x means +/−10%, unless the context dictates otherwise.

As used herein, the term "amino acid conjugate" refers to conjugates of Compound A with any suitable amino acid. Preferably, such suitable amino acid conjugates of Compound A will have the added advantage of enhanced integrity in bile or intestinal fluids. Suitable amino acids include but are not limited to glycine, taurine and acylglucuronide. Thus, the present invention encompasses the glycine, taurine and acylglucuronide conjugates of Compound A.

As used herein, the term "FXR agonist" refers to an agent that directly binds to and upregulates the activity of FXR.

As used herein, the terms "salt" or "salts" refers to an acid addition or base addition salt of a compound of the invention. "Salts" include in particular "pharmaceutical acceptable salts".

As used herein, the term "pharmaceutically acceptable" means a nontoxic material that does not interfere with the effectiveness of the biological activity of the active ingredient(s).

As used herein, the term "amino acid conjugate" refers to conjugates of the compounds, e.g. of Compound A, with any suitable amino acid. Preferably, such suitable amino acid conjugates of Compound A will have the added advantage of enhanced integrity in bile or intestinal fluids. Suitable amino acids include but are not limited to glycine, taurine and acyl glucuronide. Thus, the present invention encompasses the glycine, taurine and acyl glucuronide conjugates Compound A.

As used herein the term "prodrug" refers to compound that is converted in vivo to the compounds of the present invention. A prodrug is active or inactive. It is modified chemically through in vivo physiological action, such as hydrolysis, metabolism and the like, into a compound of this invention following administration of the prodrug to a subject. The suitability and techniques involved in making and using pro-drugs are well known by those skilled in the art. Suitable prodrugs are often pharmaceutically acceptable ester derivatives.

As used herein, the terms "patient" or "subject" refer to a human.

As used herein, the term "treat", "treating" or "treatment" of any disease or disorder refers in one embodiment to ameliorating the disease or disorder (i.e. slowing or arresting or reducing the development of the disease or at least one of the clinical symptoms or pathological features thereof). In another embodiment "treat", "treating" or "treatment" refers to alleviating or ameliorating at least one physical parameter or pathological features of the disease, e.g. including those which may not be discernible by the subject. In yet another embodiment, "treat", "treating" or "treatment" refers to modulating the disease or disorder, either physically, (e.g. stabilization of at least one discernible or non-discernible symptom), physiologically (e.g. stabilization of a physical parameter) or both. In yet another embodiment, "treat", "treating" or "treatment" refers to preventing or delaying the onset or development or progression of the disease or disorder, or of at least one symptoms or pathological features associated thereof. In yet another embodiment, "treat", "treating" or "treatment" refers to preventing or delaying progression of the disease to a more advanced stage or a more serious condition, such as e.g. liver cirrhosis; or to preventing or delaying a need for liver transplantation.

For example, treating NASH may refer to ameliorating, alleviating or modulating at least one of the symptoms or pathological features associated with NASH; e.g. hepatosteatosis, hepatocellular ballooning, hepatic inflammation and fibrosis; e.g. may refer to slowing progression, reducing or stopping at least one of the symptoms or pathological features associated with NASH, e.g. hepatosteatosis, hepatocellular ballooning, hepatic inflammation and fibrosis. It may also refer to preventing or delaying liver cirrhosis or a need for liver transplantation.

As used herein, the term "therapeutically effective amount" refers to an amount of the compound of the invention, e.g. Compound A (as hereinabove defined), which is sufficient to achieve the stated effect. Accordingly, a therapeutically effective amount of Compound A (as hereinabove defined), used for the treatment or prevention of a liver disease or disorder as hereinabove defined is an amount sufficient for the treatment or prevention of such a disease or disorder.

By "therapeutic regimen" is meant the pattern of treatment of an illness, e.g., the pattern of dosing used during the treatment of the disease or disorder.

As used herein, a subject is "in need of" a treatment if such subject would benefit biologically, medically or in quality of life from such treatment.

As used herein, the term "liver disease or disorder" encompasses one, a plurality, or all of non-alcoholic fatty liver disease (NAFLD), non-alcoholic steatohepatitis (NASH), drug-induced bile duct injury, gallstones, liver cirrhosis, alcohol-induced cirrhosis, cystic fibrosis-associated liver disease (CFLD), bile duct obstruction, cholelithiasis and liver fibrosis.

As used herein, the term NAFLD may encompass the different stages of the disease: hepatosteatosis, NASH, fibrosis and cirrhosis.

As used herein, the term NASH may encompass steatosis, hepatocellular ballooning and lobular inflammation.

As herein defined, "combination" refers to either a fixed combination in one unit dosage form (e.g., capsule, tablet, or sachet), free (i.e. non-fixed) combination, or a kit of parts for the combined administration where Compound A as herein defined, and one or more "combination partner" (i.e. the additional therapeutic agent, such as e.g. cenicriviroc or a pharmaceutically acceptable salt or solvate thereof, also referred to as or "co-agent") may be administered independently at the same time or separately within time intervals, especially where these time intervals allow that the combination partners show a cooperative, e.g. synergistic effect.

The terms "co-administration" or "combined administration" or the like as utilized herein are meant to encompass administration of the additional therapeutic agent to a single subject in need thereof (e.g. a patient), and the additional therapeutic agent are intended to include treatment regimens in which Compound A, as herein defined, and the additional therapeutic agent are not necessarily administered by the same route of administration and/or at the same time. Each of the components of the combination of the present invention may be administered simultaneously or sequentially and in any order. Co-administration comprises simultaneous, sequential, overlapping, interval, continuous administrations and any combination thereof.

The term "pharmaceutical combination" as used herein means a pharmaceutical composition that results from the combining (e.g. mixing) of more than one active ingredient and includes both fixed and free combinations of the active ingredients.

The term "fixed combination" means that the active ingredients, i.e. i) Compound A as herein defined (e.g. in free form or a pharmaceutically acceptable salt or an amino acid conjugate thereof) and ii) the additional therapeutic agent, e.g. cenicriviroc (as herein defined, e.g. cenicriviroc mesylate), are both administered to a patient simultaneously in the form of a single entity or dosage.

The term "free combination" means that the active ingredients as herein defined are both administered to a patient as separate entities either simultaneously, concurrently or sequentially with no specific time limits, and in any order, wherein such administration provides therapeutically effective levels of the two compounds in the body of the patient.

By "simultaneous administration", it is meant that Compound A, as herein defined, and the additional therapeutic agent, e.g. cenicriviroc (as herein defined, e.g. cenicriviroc mesylate), are administered on the same day. The two active ingredients can be administered at the same time (for fixed or free combinations) or one at a time (for free combinations).

According to the invention, "sequential administration", may mean that during a period of two or more days of continuous co-administration only one Compound A, as herein defined, and the additional therapeutic agent, e.g. cenicriviroc (as herein defined, e.g. cenicriviroc mesylate), is administered on any given day.

By "overlapping administration", it is meant that during a period of two or more days of continuous co-administration, there is at least one day of simultaneous administration and at least one day when only one of Compound A, as herein defined, and the additional therapeutic agent, e.g. cenicriviroc (as herein defined, e.g. cenicriviroc mesylate), is administered.

By "interval administration", it is meant a period of co-administration with at least one void day, i.e. with at least one day where neither Compound A nor the additional therapeutic agent, e.g. cenicriviroc (as herein defined, e.g. cenicriviroc mesylate, is administered.

By "continuous administration", it is meant a period of co-administration without any void day. The continuous administration may be simultaneous, sequential, or overlapping, as described above.

FXR Agonists

Compound A is 4-((N-benzyl-8-chloro-1-methyl-1,4-dihydrochromeno[4,3-c]pyrazole-3 carboxamido)methyl)benzoic acid. Compound A can be in free form or as a pharmaceutically acceptable salt, solvate, prodrug, ester and/or an amino acid conjugate thereof.

Compound A can be 4-((N-benzyl-8-chloro-1-methyl-1,4-dihydrochromeno[4,3-c]pyrazole-3 carboxamido)methyl)benzoic acid meglumine salt. In one embodiment, Compound A is 4-((N-benzyl-8-chloro-1-methyl-1,4-dihydrochromeno[4,3-c]pyrazole-3 carboxamido)methyl)benzoic acid meglumine salt Form A or Form B. In another embodiment, Compound A is 4-((N-benzyl-8-chloro-1-methyl-1,4-dihydrochromeno[4,3-c]pyrazole-3 carboxamido)methyl)benzoic acid meglumine mono-hydrate. In yet another embodiment, Compound A is 4-((N-benzyl-8-chloro-1-methyl-1,4-dihydrochromeno[4,3-c]pyrazole-3 carboxamido)methyl)benzoic acid meglumine mono-hydrate Form $H_A$ or mono-hydrate Form $H_B$.

Combination Partners

According to the invention, the additional therapeutic agent to be administered with Compound A (e.g. in free form or a pharmaceutically acceptable salt thereof) is combined (in a fixed of free combination, as hereinabove defined), with a therapeutic agent for the treatment of obesity, metabolic syndrome, cholesterol disorders or cardiometabolic diseases including diabetes, insulin resistance, dyslipidemia, liver disease. For example, Compound A can be combined with an anti-diabetic agent and/or an anti-fibrotic agent.

In one embodiment of the invention, the combination partner is a CCR2/5 inhibitor, e.g. cenicriviroc (in free form or as a pharmaceutically acceptable salt, solvate, prodrug and/or ester thereof, e.g. cenicriviroc mesylate).

C—C chemokine receptor type 2 (CCR2) and CCR5 play a role in entry of viruses such as Human Immunodeficiency Virus (HIV) into the cell, but also are important for the recruitment of immune cells to sites of injury. Inhibition of this receptors activity may have an anti-inflammatory effect. And recent data indicate that these receptors may also play a role in promoting hepatic fibrosis.

Cenicriviroc (also known as CVC) is (S,E)-8-(4-(2-butoxyethoxy)phenyl)-1-(2-methylpropyl)-N-(4-(((1-propyl-1H-imidazol-5-yl)methyl)sulfinyl)phenyl)-1, 2,3,4-tetrahydrobenzo[b]azocine-5-carboxamide. Cenicriviroc binds to and inhibits the activity of the C—C chemokine receptor type 2 (CCR2) and C—C chemokine receptor type 5 (CCR5) receptors.

Another CC2/5 inhibitor can be (S)-1-[(1S,2R,4R)-4-isopropyl(methyl)amino)-2-propylcyclohexyl]-3-(6-(trifluoromethyl)quinazolin-4-ylamino)pyrrolidin-2-one, e.g as described in WO2011/046916.

Another CC2/5 inhibitor can be BMS-813160.

Modes of Administration

The pharmaceutical composition of the invention can be formulated to be compatible with its intended route of administration (e.g. oral compositions generally include an inert diluent or an edible carrier). Other non-limiting examples of routes of administration include parenteral (e.g. intravenous), intradermal, subcutaneous, oral (e.g. inhalation), transdermal (topical), transmucosal, and rectal administration. The pharmaceutical compositions compatible with each intended route are well known in the art. Exemplary pharmaceutical compositions comprising Compound A are described in PCT/US2014/063948.

Diseases

As hereinabove defined, the fibrotic or cirrhotic disease or disorder can be a liver disease or disorder, e.g. as defined below herein, or renal fibrosis.

As hereinabove defined, the liver diseases or disorders can be cholestasis, intrahepatic cholestasis, estrogen-induced cholestasis, drug-induced cholestasis, cholestasis of pregnancy, parenteral nutrition-associated cholestasis, primary biliary cirrhosis (PBC), primary sclerosing cholangitis (PSC), progressive familiar cholestasis (PFIC), non-alcoholic fatty liver disease (NAFLD), non-alcoholic steatohepatitis (NASH), drug-induced bile duct injury, gallstones, liver cirrhosis, alcohol-induced cirrhosis, cystic fibrosis-associated liver disease (CFLD), bile duct obstruction, cholelithiasis, liver fibrosis, renal fibrosis, dyslipidemia, atherosclerosis, diabetes, diabetic nephropathy, colitis, newborn jaundice, prevention of kernicterus, veno-occlusive disease, portal hypertension, metabolic syndrome, hypercholesterolemia, intestinal bacterial overgrowth, erectile dysfunction, progressive fibrosis of the liver caused by any of the diseases above or by infectious hepatitis.

The liver diseases or disorders can also refer to liver transplantation.

In one embodiment of the invention, the pharmaceutical combination (as herein defined) is for the treatment or prevention of a fibrotic disease or disorder, e.g. a liver disease or disorder, e.g. a chronic liver disease, e.g. a liver disease or disorder selected from the group consisting of PBC, NAFLD, NASH, drug-induced bile duct injury, gallstones, liver cirrhosis, alcohol-induced cirrhosis, cystic fibrosis-associated liver disease (CFLD), bile duct obstruction, cholelithiasis, liver fibrosis. In one embodiment of the invention, the pharmaceutical combination (as herein defined) is for the treatment or prevention of fibrosis, e.g. renal fibrosis or liver fibrosis.

According to one embodiment of the invention, the liver diseases or disorders refer to NAFLD, e.g. any stages of NAFLD, e.g. any of steatosis, NASH, fibrosis and cirrhosis.

In one embodiment of the invention, there is provided a pharmaceutical combination of the invention for the improvement of liver fibrosis without worsening of steatohepatitis In another embodiment of the invention, there is provided a pharmaceutical combination of the invention for obtaining a complete resolution of steatohepatitis without worsening, e.g. improving, of liver fibrosis.

In another embodiment of the invention, there is provided a pharmaceutical combination of the invention for preventing or treating steatohepatitis and liver fibrosis.

In yet another embodiment of the invention, there is provided a pharmaceutical combination of the invention for reducing at least one of the features of the NAS score, i.e. one of hepatosteatosis, hepatic inflammation and hepatocellular ballooning; e.g. at least two features of the NAS score, e.g. hepatosteatosis and hepatic inflammation, or hepatosteatosis and hepatocellular ballooning, or hepatocellular ballooning and hepatic inflammation.

In a further embodiment of the invention, there is provided a pharmaceutical combination of the invention for reducing at least one or two features of the NAS score and liver fibrosis, e.g. for reducing hepatic inflammation and liver fibrosis, or hepatosteatosis and liver fibrosis or hepatocellular ballooning and liver fibrosis.

In yet a further embodiment of the invention, there is provided a pharmaceutical combination of the invention for treating or preventing, stage 3 fibrosis to stage 1 fibrosis, e.g. stage 3 and/or stage 2 and/or stage 1 fibrosis.

Patients

According to the invention, the patients receiving the combination of the invention can be affected or at risk of a fibrotic disease or disorder, e.g. a liver disease or disorder, e.g. as hereinabove defined.

In some embodiments of the invention, the patient is obese or overweight

In other embodiments of the invention, the patient may be a diabetic patient, e.g. may have type 2 diabetes. The patient may have high blood pressure and/or high blood cholesterol level.

Dosing Regimens

Depending on the patient general condition, the targeted disease or disorder and the stage of such disease or disorder, the dosing regimen, i.e. administered doses and/or frequency of each component of the pharmaceutical combination may vary.

The frequency of dosing of Compound A, as herein defined, and optionally the additional therapeutic agent, e.g as a fixed dose combination, may be once per day, twice per day, three times per day, four times per day, five times per day, six times per day, or every two days, every three days or once per week, e.g. once a day.

According to the invention, Compound A and the additional therapeutic agent may not be administered following the same regimen, i.e. may not be administered at the same frequency and/or duration and/or dosage, e.g. at the same frequency and/or dosage. This can be the case e.g. for free combinations. As one example, Compound A can be administered one a day and the additional therapeutic agent, e.g. a CCR2/5 inhibitor, e.g. cenicriviroc (in free form or as a pharmaceutically acceptable salt, solvate, prodrug and/or ester thereof, e.g. cenicriviroc mesylate) twice per day, or reciprocally.

In one embodiment, e.g. in case of simultaneous administration, Compound A is administered one to four times per day, and the additional therapeutic agent, e.g. cenicriviroc (in free form or as a pharmaceutically acceptable salt, solvate, prodrug and/or ester thereof) is administered from one to four times per day.

In one embodiment of the invention, the co-administration is carried out for at least one week, at least one month, at least 6 weeks, at least three months, at least 6 months, at least one year. For example, the pharmaceutical combination of the invention is administered lifelong to the patient. The frequency of administration, and/or the doses of the Compound A, and optionally of the additional therapeutic agent, may vary during the whole period of administration.

During the treatment, there can be one or more periods of time, e.g. days, during which Compound A, and optionally the additional therapeutic agent, e.g. a CCR2/5 inhibitor, are not administered to the patient (i.e. periods, e.g. days, void of combination treatment), or during which only one drug amongst the FXR agonist or the additional therapeutic agent is administered to the patient.

In case of a sequential co-administration, Compound A, as herein defined, may be administered prior the additional therapeutic agent, or reciprocally. The time interval between administration of Compound A and of the additional therapeutic agent may vary from a few minutes to a few days, e.g. a few minutes, e.g. a few hours, e.g. 1 day to 1 week.

The dosing frequency will depend on, inter alia, the phase of the treatment regimen.

According to the invention, Compound A (as hereinabove defined, e.g. in free form or as a pharmaceutically acceptable salt thereof) is administered at a dose of about 5 mg to about 750 mg. Such doses may be for oral administration of Compound A. Such doses may be for daily administration of Compound A, twice daily administration or every two days administration, e.g. for daily oral administration.

In some aspects, Compound A (as hereinabove defined, e.g. in free form or as a pharmaceutically acceptable salt thereof) is administered at a dose of e.g about 15 mg, e.g about 20 mg, e.g about 30 mg, e.g about 40 mg, e.g about 50 mg, e.g. about 60 mg, e.g about 80 mg, e.g. about 100 mg, e.g. about 120 mg, e.g. about 140 mg, e.g. about 150 mg, e.g about 180 mg, e.g about 200 mg, e.g about 220 mg, e.g about 250 mg. Such doses may be for oral administration of Compound A, e.g. for once daily oral administration. Such doses may be for daily administration of Compound A, twice daily administration or every two days administration, e.g. for daily oral administration.

In some aspects, Compound A (as herein above defined, e.g in free form or as a pharmaceutically acceptable salt thereof) is administered at a dose in a range of about 15 mg to about 250 mg, e.g about 25 mg to about 250 mg, e.g.

about 100 mg to about 250 mg, e.g. about 10 mg to about 200 mg; e.g. about 100 mg to about 200 mg; e.g. about 30 mg to about 200 mg, e.g. about 50 mg to about 200 mg. Such doses may be for daily administration of Compound A, twice daily administration or every two days administration, e.g. for daily oral administration. These doses can be in particular for meglumine salt of Compound A.

In some embodiments, Compound A as herein defined (e.g. in free form or a pharmaceutically acceptable salt thereof) is administered at a dose of about 15 mg delivered orally, about 20 mg delivered orally, about 25 mg delivered orally, about 50 mg delivered orally, about 60 mg delivered orally, about 80 mg delivered orally, about 100 mg delivered orally, about 120 mg delivered orally, about 140 mg delivered orally, about 150 mg delivered orally, about 180 mg delivered orally, about 200 mg delivered orally, about 220 mg delivered orally, about 250 mg delivered orally. Such doses may be particularly adapted for patients of weight from about 50 kg to about 120 kg, e.g. from about 70 kg to about 100 kg. These doses can be in particular for meglumine salt of Compound A.

In some embodiments, Compound A as herein defined (e.g. in free form or a pharmaceutically acceptable salt thereof) is administered at a dose in a range of about 50 mg/day, e.g. about 60 mg/day, e.g about 80 mg/day, e.g. about 100 mg/day, e.g. about 120 mg/day, e.g. about 140 mg/day, e.g. about 150 mg/day, e.g. about 180 mg/day, e.g. about 200 mg/day, e.g. about 220 mg/day, e.g. about 250 mg/day. Such regimens may be delivered orally. These doses can be in particular for meglumine salt of Compound A.

In some embodiments, Compound A as herein defined (e.g. in free form or a pharmaceutically acceptable salt thereof), is administered at a dose of about 50 mg twice daily, about 60 mg twice daily, about 80 mg twice daily, about 100 mg twice daily, about 140 mg twice daily, about 150 mg twice daily, about 180 mg twice daily, about 200 mg twice daily, about 220 mg twice daily, about 250 mg twice daily. Such regimens may be delivered orally. These doses can be in particular for meglumine salt of Compound A.

In some embodiments, there is provided Compound A at a daily dose of about 50 mg, of about 100 g, of about 150 mg or of about 200 mg.

According to the invention, the CCR2/5 inhibitor, e.g. cenicriviroc (as hereinabove defined, e.g. cenicriviroc mesylate) is administered at a dose of about 50 mg, e.g. about 60 mg, e.g about 80 mg, e.g. about 100 mg, e.g. about 120 mg, e.g. about 140 mg, e.g. about 150 mg, e.g about 180 mg, e.g about 200 mg, e.g about 220 mg, e.g about 250 mg. Such doses may be for oral administration of CCR2/5 inhibitor, e.g. cenicriviroc (as hereinabove defined, e.g. cenicriviroc mesylate). Such doses may be for daily administration of CCR2/5 inhibitor, e.g. cenicriviroc (as hereinabove defined, e.g. cenicriviroc mesylate), twice daily administration or every two days administration, e.g. for daily oral administration.

In some aspects, the CCR2/5 inhibitor, e.g. cenicriviroc (as herein above defined, e.g cenicriviroc mesylate) is administered at a dose in a range of about 30 mg to about 250 mg, e.g about 50 mg to about 250 mg, e.g. about 100 mg to about 250 mg, e.g. about 10 mg to about 200 mg; e.g. about 100 mg to about 200 mg; e.g. about 30 mg to about 200 mg, e.g. about 50 mg to about 200 mg. Such doses may be for oral administration of CCR2/5 inhibitor, e.g. cenicriviroc (as hereinabove defined, e.g. cenicriviroc mesylate). Such doses may be for daily administration of CCR2/5 inhibitor, e.g. cenicriviroc (as hereinabove defined, e.g. cenicriviroc mesylate), twice daily administration or every two days administration, e.g. for daily oral administration.

In some embodiments, the CCR2/5 inhibitor, e.g. cenicriviroc (as hereinabove defined, e.g. cenicriviroc mesylate), is administered at a dose of about 50 mg delivered orally, about 60 mg delivered orally, about 80 mg delivered orally, about 100 mg delivered orally, about 120 mg delivered orally, about 140 mg delivered orally, about 150 mg delivered orally, about 180 mg delivered orally, about 200 mg delivered orally, about 220 mg delivered orally, about 250 mg delivered orally. Such doses may be particularly adapted for patients of weight between 50 and 120 kg, e.g. 70 and 100 kg.

In some embodiments, the CCR2/5 inhibitor, e.g. cenicriviroc (as hereinabove defined, e.g. cenicriviroc mesylate), is administered at a dose in a range of about 50 mg/day, e.g. about 60 mg/day, e.g about 80 mg/day, e.g. about 100 mg/day, e.g. about 120 mg/day, e.g. about 140 mg/day, e.g. about 150 mg/day, e.g. about 180 mg/day, e.g. about 200 mg/day, e.g. about 220 mg/day, e.g. about 250 mg/day. Such regimens may be delivered orally. Such regimens may be particularly adapted for patients of weight between 50 and 120 kg, e.g. 70 and 100 kg.

In some embodiments of the invention, the CCR2/5 inhibitor, e.g. cenicriviroc (as hereinabove defined, e.g. cenicriviroc mesylate), is administered at a dose of about 50 mg twice daily, about 60 mg twice daily, about 80 mg twice daily, about 100 mg twice daily, about 140 mg twice daily, about 150 mg twice daily, about 180 mg twice daily, about 200 mg twice daily, about 220 mg twice daily, about 250 mg twice daily. Such regimens may be delivered orally.

In one embodiment of the invention, the pharmaceutical combination, e.g fixed or free combination, comprises i) about 100 mg to about 250 mg of Compound A (as hereinabove defined, e.g. in free form or as a pharmaceutically acceptable salt thereof, e.g. meglumine salt) and ii) about 100 to about 250 mg of cenicriviroc (as hereinabove defined, e.g. cenicriviroc mesylate). For example, the pharmaceutical combination, e.g fixed or free combination, comprises i) about 100 mg of Compound A (as hereinabove defined, e.g. in free form or as a pharmaceutically acceptable salt thereof) and ii) about 150 mg of cenicriviroc (as hereinabove defined, e.g. cenicriviroc mesylate).

In other embodiments, there are provided pharmaceutical combinations, containing, separate or together, (i) Compound A as herein defined (e.g. in free form or a pharmaceutically acceptable salt thereof, e.g. meglumine salt); and (ii) a CCR2/5 inhibitor, e.g. cenicriviroc (as hereinabove defined, e.g. cenicriviroc mesylate), for simultaneous or sequential administration, wherein the ratio (mg/mg) of Compound A to CCR2/5 inhibitor, e.g. cenicriviroc (as hereinabove defined), is about 0.5:1 to about 10:1, e.g. about 0.5:1 to about 8:1, e.g. about 0.5:1 to about 5:1; about 0.5:1 to about 3:1, e.g. about 1:1 to about 5:1, e.g. about 1:1 to about 3:1, e.g. about 1:1 to about 2:1, e.g. about 1:1. These ratios are particularly adapted for pharmaceutical combinations comprising Compound A (in free form or a pharmaceutically acceptable salt thereof, e.g. meglumine salt) and cenicriviroc (as hereinabove defined, e.g. cenicriviroc mesylate).

In specific embodiments of the inventions, Compound A as herein defined (e.g. in free form or a pharmaceutically acceptable salt thereof, e.g. meglumine salt), is administered for a period of 3 months to lifelong, e.g. 6 months to lifelong, e.g. 1 year to lifelong, e.g. fora period of 3 months to 1 year, e.g. 6 months to lifelong, e.g. for a period of 3 months, 6 months or 1 year or for lifelong.

Kits for the Treatment of Fibrotic Disease or Disorder, e.g. a Liver Disease or Disorder Accordingly, there are provided pharmaceutical kits comprising: a) Compound A (as hereinabove defined, e.g. in free form or as a pharmaceutically acceptable salt thereof; b) an additional therapeutic agent, e.g. a CCR2/5 inhibitor, e.g. cenicriviroc (as hereinabove defined, e.g. cenicriviroc mesylate); and c) means for administering Compound A and the additional therapeutic agent (e.g. cenicriviroc (e.g. cenicriviroc mesylate), to a subject affected by a liver disease or disorder; and optionally d) instructions for use.

In one embodiment of the invention, there is provided a combination package comprising a) at least one individual dose of Compound A as herein defined, e.g. in free form or as a pharmaceutically acceptable salt thereof; and b) at least one individual dose of an additional therapeutic agent as hereinabove defined, e.g. a CCR2/5 inhibitor, e.g. cenicriviroc (as hereinabove defined, e.g. cenicriviroc mesylate). The combination package may further comprise instructions for use.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

Example 1: In Vivo Efficacy Study of Compound A in the STAM Model of Non-alcoholic Steatohepatitis (Treatment period: 6 to 9 wks and 9-12 weeks)

The study involves 14-day-pregnant C57BL/6 mice. NASH was established by a single subcutaneous injection of 200 μg streptozotocin (Sigma, USA) after birth and feeding with a high fat diet (HFD, 57% kcal fat, CLEA Japan, Japan) ad libitum after 4 weeks of age (day 28±2). Randomization of NASH mice into groups of 12 mice at 6 weeks of age (day 42±2) and groups of 12 mice at 9 weeks of age (day 63±2), the day before the start of treatment, respectively. NASH animals were dosed from age 6-9 weeks (Study 1), or from age 9-12 weeks (Study 2) with either: vehicle, Compound A, OCA or Compound A. A non-disease vehicle-control group of was included in both Study 1 and Study 2. These animals were fed with a normal diet (CE-2; CLEA Japan) ad libitum.

PK samples were collected and stored at ≤−60° C. Animals were dosed according to the dosing schedule below. Each animal was sacrificed 5 hours after last morning dose on the last day of study treatment (the evening dose of cenicriviroc or vehicle was administered that day due to sacrifice).

Measurements:
The following parameters were measured or monitored daily: individual body weight, survival, clinical signs and behavior of mice.

Pharmacokinetic measurements: PK samples were collected from 4 animals per time point per compound. PK samples were for Compound A at hours 1 and 24 on Day 6 (n=4 per timepoint) for both monotherapy and combination groups. PK samples were taken for Cenicriviroc on Day 10 at hours 2 and 12 (n=4 per timepoint) for both monotherapy and combination groups.

Only one PK sample was collected per animal using the first 8 animals per group, per the schedule below:

Mice were sacrificed at 9 weeks of age (study 1) or at 12 weeks of age (study 2). The 8 NASH animals that that did not receive any treatment or vehicle were sacrificed at week 9 as a 'baseline' in order for comparisons of any fibrosis regression events observed in treated animals.

The following samples were collected: plasma, liver (fresh liver samples for gene expression analysis were collected at 5 hr post the last morning (AM) dose for each animal), stool. Organ weight was measured.

The following biochemical assays were performed: Non-fasting blood glucose in whole blood by Life Check (Eidia, Japan); serum ALT by FUJI DRI-CHEM (Fujifilm, Japan); serum triglyceride; serum MCP-1, RANTES (CCLS) and MIP-1a/MIP-1 quantification by a commercial ELISA kit; liver triglyceride by Triglyceride E-test kit (Wako, Japan); liver hydroxyproline quantification by hydrolysis method; histological analyses for liver section; HE staining and estimation of NAFLD Activity score; Sirius-red staining and estimation of fibrosis area (with and without perivascular space subtracted); oil red staining and estimation of fat deposition area; F4/80 immunohistochemistry staining and estimation of inflammation area; alpha-SMA immunohistochemistry staining and estimation of α-SMA positive area Gene expression assays using total RNA from the liver.

Real-time RT-PCR analyses were performed for: MCP-1, MIP-1α/β, RANTES, Emr1, CD68, TGF-β1, CCR2/5, TIMP-1, Cola1A1, TNF, IL-10, MMP-9, α-SMA and CX3CR1/CX3CL1, SHP (small heterodimer partner), BSEP (bile salt export pump), Cyp8b1.

Statistical tests were performed using one-way ANOVA followed by Dunnett's test and the Mann-Whitney test, as appropriate, for the multiple group comparisons. P values <0.05 are considered statistically significant.

Results:

NAS score:

Study 1:

| Treatment Group | NAS (mean +/− SD) |
| --- | --- |
| Non-diseased animal | 0.0 ± 0.0 |
| STAM - vehicle | 4.8 ± 0.7 |
| Compound A | 2.7 ± 1.1 |

Study 2.

| Treatment Group | NAS (mean +/− SD) |
| --- | --- |
| Non-diseased animal | 0.0 ± 0.0 |
| STAM - vehicle | 4.9 ± 1.1 |
| Baseline | 3.0 ± 2.0 |
| Compound A | 2.7 ± 1.1 |

In both studies 1 and 2, Compound A treatment showed a significant reduction in NAS compared with the STAM-Vehicle group.

Inflammatory Infiltrates

Study 1:

|  | Score (number of animals/group) | | | |
| --- | --- | --- | --- | --- |
| Treatment Group | 0 | 1 | 2 | 3 |
| Non-diseased animal | 10 | 0 | 0 | 0 |
| STAM - vehicle | 0 | 2 | 4 | 3 |
| Compound A | 7 | 2 | 1 | 0 |

Study 2

|  | Score (number of animals/group) | | | |
| --- | --- | --- | --- | --- |
| Treatment Group | 0 | 1 | 2 | 3 |
| Non-diseased animal | 12 | 0 | 0 | 0 |
| STAM - vehicle | 0 | 0 | 3 | 5 |
| Baseline | 0 | 1 | 4 | 3 |
| Compound A | 3 | 1 | 4 | 2 |

In both studies 1 and 2, Compound A treatment showed a significant reduction of Inflammatory infiltrates compared with the STAM-Vehicle group.

Ballooning

Study 1

| Treatment Group | NAS (mean +/− SD) |
| --- | --- |
| Non-diseased animal | 0.0 ± 0.0 |
| STAM - vehicle | 1.6 ± 0.5 |
| Compound A | 1.3 ± 0.8 |

|  | Score (number of animals/group) | | |
| --- | --- | --- | --- |
| Treatment Group | 0 | 1 | 2 |
| Non-diseased animal | 10 | 0 | 0 |
| STAM - vehicle | 0 | 4 | 5 |
| Compound A | 2 | 3 | 5 |

Study 2

| Treatment Group | NAS (mean +/− SD) |
| --- | --- |
| Non-diseased animal | 0.0 ± 0.0 |
| STAM - vehicle | 1.3 ± 0.5 |
| Baseline | 1.4 ± 0.5 |
| Compound A | 0.7 ± 0.8 |

|  | Score (number of animals/group) | | |
| --- | --- | --- | --- |
| Treatment Group | 0 | 1 | 2 |
| Non-diseased animal | 12 | 0 | 0 |
| STAM - vehicle | 0 | 6 | 2 |
| Baseline | 0 | 5 | 3 |
| Compound A | 5 | 3 | 2 |

In both studies, Compound A treatment showed a trend for the reduction of ballooning compared with the STAM-Vehicle group.

Fibrosis

Study 1

| Treatment Group | NAS (mean +/− SD) |
| --- | --- |
| Non-diseased animal | 0.16 ± 0.06 |
| STAM - vehicle | 0.65 ± 0.22 |
| Compound A | 0.51 ± 0.25 |

Study 2

| Treatment Group | NAS (mean +/− SD) |
| --- | --- |
| Non-diseased animal | 0.26 ± 0.06 |
| STAM - vehicle | 0.70 ± 0.21 |
| Baseline | 0.68 ± 0.16 |
| Compound A | 0.55 ± 0.32 |

In both studies, Compound A treatment showed a trend for the reduction of the fibrosis area compared with the STAM-Vehicle group.

Example 2: Compound A and OCA Have Been Tested in the Same STAM Mouse Model of NASH than Described in Example 1

NASH was induced for 6 weeks prior to treatment with the indicated compound (and dose). Then, they have been treated with the indicated compound for 3 weeks prior to sacrifice.

NAFLD Activity Score from H&E stained liver sections from STAM disease (NASH) animals treated for 3 weeks with the indicated compound or vehicle. Disease was initiated in animals for 6 weeks prior to dosing and then animals were treated with Vehicle-1, Vehicle-2, Compound A (3 to 30 mg/kg) or OCA (25 mg/kg) for 3 weeks. NAS was determined by the method of Kleiner (Kleiner et al. 2005).

Sirius red stained liver sections from STAM disease (NASH) animals treated for 3 weeks with the indicated compound or vehicle. Disease was initiated in animals for 6 weeks prior to dosing and then animals were treated with Vehicle-1, Vehicle-2, Compound A (3 to 30 mg/kg) or OCA (25 mg/kg) for 3 weeks. Quantitative analysis of Sirius Red sections were performed using ImageJ software.

The results are shown in FIGS. 1 and 2.

Compound A has reduced hepatic steatosis, lobular inflammation, hepatocellular ballooning and fibrosis to a greater extent than OCA.

Example 3: Rat ANIT-Induced Cholestasis Chronic Treatment Model

The efficacious concentration of Compound A was determined by PK/PD modeling from the rat ANIT-induced cholestasis chronic treatment model.

Compound A has improved hepatobiliary injury indicators in the severe rat ANIT-induced cholestasis model: ALT, AST and GGT were significantly reduced by 75, 80 and 85% respectively when Compound A has been used at 1.5 mg/kg. Compound A reduced the ANIT-induced histologic alterations in the liver, consistent with the hematological and biochemical indicators of hepatobiliary injury and cholestasis.

Example 4: Human Study

Methods: SAD: Subjects received 5 to 750 mg of Compound A (7 cohorts: 6 active, 2 placebo); subjects from one cohort returned for a second dosing cycle with a high-fat meal (3 active, 1 placebo). MAD: Subjects received 5 to 250 mg of Compound A daily for 14 days (5 cohorts; 6 active, 2 placebo). All adverse events (AEs) were captured, and plasma levels of Compound A and PD biomarkers were determined pre- and post-dosing at various time points.

Results: Overall, 95 subjects completed the scheduled dosing. Compound A was well tolerated at the maximum doses tested (750 mg SAD and 250 mg MAD). No severe drug-related AEs were reported in any cohort. SAD: At 5-750 mg doses, median plasma Tmax and mean t1/2 were 1.75-3 h and 11.7-23.5 h, respectively, with mean Cmax of 177-12700 ng/mL. With high-fat meal, median Tmax of Compound A increased to 4 h; AUC decreased by 26% and Cmax by 58%. MAD: Steady-state was reached by Day 5 with a mild accumulation ratio. On Day 14, a dose-dependent increase in plasma FGF19 levels was observed with a median Cmax of 979 pg/mL at 250 mg Compound A. A decline in serum C4 and total bile acid (TBA) levels was also observed over a similar dose range of Compound A. Serum FGF15 levels were increased with Compound A treatment in a dose-dependent manner.

The data from this clinical trial as well as preclinical evidence presented above show that Compound A at daily doses of 5 mg to 750 mg to be safe and pharmacological active for treatment of liver disease, e.g NASH. Furthermore, FGF19 continues to rise with increasing Compound A doses even beyond 250 mg. No SAEs have been attributed to Compound A in the Human study at daily doses up to 250 mg for 14 days. Based on the data from this trial, the lowest pharmacologically active dose (PAD) PAD in humans for Compound A was estimated to be a range of 15-45 mg assuming a 70 kg body weight.

We claim:

1. A method for treating diabetic nephropathy in a human, comprising administering to a human in need thereof, a daily dose of about 50 mg to about 200 mg of 4-((N-benzyl-8-chloro-1-methyl-1,4-dihydrochromeno[4,3-c]pyrazole-3-carboxamido)methyl)benzoic acid or a pharmaceutically acceptable salt thereof.

2. The method of claim 1, wherein said dose is about 50 mg of 4-((N-benzyl-8-chloro-1-methyl-1,4-dihydrochromeno[4,3-c]pyrazole-3-carboxamido)methyl)benzoic acid meglumine salt.

3. The method of claim 1, wherein said dose is about 100 mg of 4-((N-benzyl-8-chloro-1-methyl-1,4-dihydrochromeno[4,3-c]pyrazole-3-carboxamido)methyl)benzoic acid meglumine salt.

4. The method of claim 1, wherein said dose is about 50 mg of 4-((N-benzyl-8-chloro-1-methyl-1,4-dihydrochromeno[4,3-c]pyrazole-3 carboxamido)methyl)benzoic acid meglumine mono-hydrate.

5. The method of claim 1, wherein said dose is about 100 mg of 4-((N-benzyl-8-chloro-1-methyl-1,4-dihydrochromeno[4,3-c]pyrazole-3 carboxamido)methyl)benzoic acid meglumine mono-hydrate.

6. The method of claim 1, wherein said human is diabetic.

* * * * *